(12) United States Patent
Prox et al.

(10) Patent No.: US 8,237,118 B2
(45) Date of Patent: Aug. 7, 2012

(54) PARTIAL OVOIDAL FAIMS ELECTRODE

(75) Inventors: Todd Prox, Interlachen, FL (US);
Marilyn Prieto, Gainesville, FL (US);
Jennifer Bryant, Gainesville, FL (US);
Richard Alan Yost, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 293 days.

(21) Appl. No.: 12/195,867

(22) Filed: Aug. 21, 2008

(65) Prior Publication Data
US 2010/0044557 A1    Feb. 25, 2010

(51) Int. Cl.
*H01J 49/26* (2006.01)

(52) U.S. Cl. ........ 250/290; 250/281; 250/292; 250/293; 250/396 R; 250/398

(58) Field of Classification Search ............... 250/396 R, 250/398, 281, 282, 286, 288, 290, 291, 292, 250/293, 294, 295, 296, 297, 285
See application file for complete search history.

(56) References Cited

U.S. PATENT DOCUMENTS

| | | | |
|---|---|---|---|
| 5,420,424 A | 5/1995 | Carnahan et al. | |
| 6,713,758 B2 | 3/2004 | Guevremont et al. | |
| 6,753,522 B2 | 6/2004 | Guevremont et al. | |
| 7,148,474 B2 | 12/2006 | Tang et al. | |
| 7,274,014 B2 | 9/2007 | Guevremont et al. | |
| 2003/0213899 A9* | 11/2003 | Guevremont et al. | 250/281 |
| 2005/0151072 A1* | 7/2005 | Guevremont et al. | 250/282 |
| 2005/0258363 A1* | 11/2005 | Syms | 250/292 |
| 2008/0067366 A1* | 3/2008 | Belford | 250/294 |
| 2008/0315085 A1* | 12/2008 | Belford et al. | 250/290 |

FOREIGN PATENT DOCUMENTS

| | | |
|---|---|---|
| WO | WO 00/08455 | 2/2000 |
| WO | WO 00/08457 | 2/2000 |
| WO | WO 01/69216 | 9/2001 |

OTHER PUBLICATIONS

Prieto, M., et al., "Design of a Hemispherical FAIMS Cell," *56th ASMS Conference on Mass Spectrometry*, Jun. 1-5, 2008, Denver, Colorado.

(Continued)

*Primary Examiner* — David A Vanore
*Assistant Examiner* — Nicole Ippolito
(74) *Attorney, Agent, or Firm* — Saliwanchik, Lloyd, Eisenschenk

(57) ABSTRACT

A partial ovoidal FAIMS apparatus for separating ions is presented with inner and outer electrodes that have geometrically matched convex and concave partial ovoidal surfaces, respectively, that share at least one common defining axis and display a nearly constant displacement between the opposing surfaces. The ovoidal surfaces can be that of an egg shaped ovoid, an ellipse, or a sphere. The apparatus can have at least one ion inlet and an ion outlet where the outlet is on or as near as possible to a point on the defining axis in the outer electrode and the inlet or inlets are on, near, or symmetrically disposed about the defining axis of the ovoidal surfaces. Electrical contacts to the electrodes permit the application of an asymmetric waveform and a compensation voltage to at least one of the electrodes. The electrodes are positioned, stabilized, and insulated from each other by a base plate.

12 Claims, 14 Drawing Sheets

OTHER PUBLICATIONS

Guevremont, R., et al., "Comparison of Experimental and Calculated Peak Shapes for Three Cylindrical Geometry FAIMs Prototypes of Differing Electrode Diameters," *Journal of the American Society for Mass Spectrometry*, 2005, pp. 349-362, vol. 16, No. 3.

Shvartsburg, A. A., et al., "Optimization of the Design and Operation of FAIMS Analyzers," *Journal of the American Society for Mass Spectrometry*, 2005, pp. 2-12, vol. 16, No. 1.

Shvartsburg, A. A., et al., "Modeling the Resolution and Sensitivity of FAIMS Analyses," *Journal of the American Society for Mass Spectrometry*, 2004, pp. 1487-1498, vol. 15, No. 10.

Guevremont, R., et al., "Atmospheric Pressure Ion Trapping in a Tandem FAIMS-FAIMS Coupled to a TOFMS: Studies with Electrospray Generated Gramicidin S Ions," *Journal of the American Society for Mass Spectrometry*, 2001, pp. 1320-1330, vol. 12, No. 12.

Guevremont, R., et al., "Compensation Voltage (CV) Peak Shapes Using a Domed FAIMS with the Inner Electrode Translated to Various Longitudinal Positions," *Journal of the American Society for Mass Spectrometry*, 2005; pp. 948-956, vol. 16, No. 6.

* cited by examiner

PARTIAL OVOIDAL FAIMS ELECTRODE

BACKGROUND OF THE INVENTION

Ion mobility spectrometry (IMS) is an important technique for the detection of narcotics, explosives, and chemical warfare agents because of its high sensitivity and amenability to miniaturization for field-portable applications. In IMS, gas-phase ions migrate in a drift tube in the presence of a constant electric field. Ions are separated by differences in their drift velocities. For electric field strengths that are relatively low, an ion's drift velocity depends on the applied electric field strength and the mobility, K, which is independent of the applied electric field and experimentally determined. The ions travel through a bath gas at a sufficiently high pressure that allows the ions to rapidly achieve a constant velocity when driven by the force of a constant electric field, which contrasts to migration in a mass spectrometry where ions accelerate in a constant electric field at low pressure.

At high electric field strengths the ion drift velocity is not directly proportional to the applied field and the mobility, $K_h$, is not a constant, but rather dependent on the applied electric field. This dependence has been exploited to develop high field asymmetric waveform ion mobility spectrometry (FAIMS) where ions are separated by a difference in their mobility at high field strength, $K_h$, relative to their mobility at low field strength, K. In FAIMS, ions are separated due to the dependent behavior of $K_h$ as a function of the applied electric field strength.

A FAIMS spectrometer has an analyzer region defined by the space between two electrodes. One electrode is maintained at a selected dc voltage, often at ground potential, while the second electrode has an asymmetric waveform V(t) imposed upon it that is a repeating pattern of a short, $t_h$, high voltage, $V_h$, periods and longer, $t_1$, lower voltage, $V_1$, periods such that $V_h t_h + V_1 t_1 = 0$ for each complete cycle of the waveform. The peak voltage during the high voltage portion of the waveform is called the "dispersion voltage" or DV.

Ions to be separated are entrained in a stream of gas flowing through the FAIMS analyzer region. The net motion of an ion is the sum of an axial x-axis component due to the stream of gas and a transverse y-axis component due to the applied electric field. The distance traveled by an ion during the high voltage portion of the waveform is given by $d_h = K_h E_h t_h$ where $E_h$ is the applied field. Likewise, during the low voltage portion of the asymmetric waveform, $d_1 = KE_1 t_1$. As $E_h t_h$ and $E_1 t_1$ are equal in magnitude the net displacement along the y-axis occurs because of the difference in $K_h$ and K. This transverse drift is compensated by applying a constant voltage to the first electrode, the "compensation voltage" or CV. Hence, where multiple ions are present, only an ion whose drift is compensated can arrive at a detector for an appropriate combination of DV and CV. Analysis can be carried out by changing CV over time.

Various designs using curved electrode bodies have been disclosed. Buryakov et al. *Int. J. Mass Spectrom. Ion Processes,* 128, 143 (1993) disclosed the first FAIMS device with planar electrodes. The electric field between the planar electrodes is uniform, allowing ions to diffuse laterally. Because there is a lack of ion focusing, poor ion transmission into the narrow outlet, which is often the entrance to a mass spectrometer, affects sensitivity. The use of curved electrodes produces a two-dimensional atmospheric pressure ion focusing effect that achieves greater ion transmission efficiencies. For example, Carnahan et al. U.S. Pat. No. 5,420,424, describes a device where two cylindrical electrodes are used where one electrode is concentrically located within a tubular electrode and the ions are transmitted parallel to the central axis of the cylinders. Guevremont et al., WO 00/08455, describe a domed-FAIMS analyzer where a cylindrical inner electrode has a curved surface terminus proximate an ion outlet orifice to an analyzer region. The application of an asymmetric waveform to the inner electrode has an additional ion-focusing action that extends around the spherically shaped terminus of the inner electrode that causes the selected ions to be directed radially inwardly within the region proximate the inner electrode terminus. The inward drift is balanced by the force of the carrier gas flow and the focusing action of the applied electric fields to effectively capture the selected ions. When all forces acting upon the ions are balanced, the ions are effectively accumulated near the terminus of the inner electrode by forces of the flowing gas, or by the focusing effect of the electric fields of the FAIMS mechanism. This three-dimensional ion trap can be used in a near-trapping mode as disclosed in Guevremont et al., WO 00/08457, where the accumulated ions are leaked to an outlet orifice by a flow of gas towards the ion-outlet orifice as a narrow collimated beam where the gas flow is induced by a smaller orifice leading to the vacuum system of a mass spectrometer. This tandem domed-FAIMS/MS device is capable of detecting and identifying ions at part-per-billion levels.

Guevremont et al., WO 1/69216 disclose a "side-to-side" FAIMS. In this design the ions are transmitted around the circumference of the inner cylindrical electrode. The ion inlet and the ion outlet of a side-to-side FAIMS device are disposed, one opposing the other, within a surface of the outer electrode. An ion is selectively transmitted through the curved analyzer region between the ion inlet and the ion outlet along a continuously curving ion flow path perpendicular to the central axis of the cylinders. The ions travel approximately fifty percent of the circumference of the inner electrode and are partitioned between two streams traveling in opposite directions around the inner electrode, effective reducing the ion density within the analyzer region, reducing the ion-ion repulsion space charge effect, and allowing a reduction of the travel distance to improve the ion transmission efficiency. However, in this design the ions are not focused in a direction parallel to the central axis of the cylindrical electrodes and an inner cylinder with a small radius is required to produce a strongly focused field, which can result in ion transit times that are insufficient to separate mixtures of different ions.

Guevremont et al. U.S. Pat. No. 6,713,758 discloses a spherical side-to-side FAIMS that overcomes many of the limitations of the cylindrical side-to-side FAIMS. In this design, the cylindrical electrodes are replaced with an outer electrode with a spherical cavity and an inner electrode that is a sphere. Unlike the cylindrical side-to-side design, where the electrical field varies radially as a function of 1/r, the spherical design has improved focusing capabilities as the electric field varies as a function of $1/r^2$. The spherical design restores the advantage of the domed-FAIMS analyzer absent in the cylindrical side-to-side FAIMS, because the gases converge to the ion outlet and all of the ions travel a nearly identical distance from the inlet to the outlet.

Nevertheless, the spherical side-to-side FAIMS has limitations that have hindered its commercial development as design and construction of a practical spherical cell is a daunting task. For example, the suspension of a central spherical electrode exactly at the center of a spherical cavity while delivering several thousand volts of RF to the central electrode is extremely difficult. Many designs fail to provide the precise, accurate, and rigid centering required of the electrode.

BRIEF SUMMARY OF THE INVENTION

An apparatus for separating ions has at least one ion inlet and an ion outlet to introduce and remove ions from an analyzer region defined by the space between an inner concave partial ovoidal surface of an outer electrode concentric with an outer convex partial ovoidal surface of an inner electrode where there is a nearly constant displacement between the ovoidal surfaces. An electrical contact on at least one of the electrodes allows the application of a compensation voltage between the electrodes and an electrical contact on at least one of the electrodes allows the application of an asymmetric waveform to at least one of the electrodes during use, wherein at least one of said ions is selectively transmitted through said analyzer region. A base plate is used to fix the electrodes and to electrically insulate the electrodes from each other. The ovoidal surfaces can be spherical surfaces, elliptical surfaces, or egg shaped ovoidal surfaces.

In embodiments of the invention where the partial ovoidal surfaces are greater than hemi-ovoidal surfaces, the ion inlet or ion inlets can reside in a portion of the outer electrode and the ion outlet can reside in another portion of the outer electrode with the ion outlet and ion inlet are on a common defining axis of the ovoidal surfaces or a plurality of ion inlets are situated equidistant about the common defining axis.

In embodiments of the invention where the partial ovoidal surfaces are less than or equal to hemi-ovoidal surfaces, the ion inlet and ion outlet can reside in portions of the outer electrode with the ion outlet and ion inlet are on a line parallel to a common defining axis of the ovoidal surfaces or a plurality of ion inlets are situated equidistant about the line parallel to the common defining axis.

In embodiments of the invention where the partial ovoidal surfaces are less than or equal to hemi-ovoidal surfaces the ion inlet and ion outlet can reside in portions of the base plate. In an embodiment of the invention the ion inlet and ion outlet can be perpendicular to a common defining axis of a hemi-ovoidal surfaces or a line parallel to the common defining axis of a less than hemi-ovoidal surfaces.

In other embodiments of the invention, the apparatus can have an ion inlet with a multiplicity of ion inlet channels exiting into the analyzer region at a plane of truncation of the partial ovoidal surfaces at the base plate with the ion outlet residing in a portion of the outer electrode on the common defining axis of the ovoidal surfaces that is perpendicular to the plane of truncation. The ion inlet channels can be at least partially through said base plate, in a portion of the inner electrode coplanar with the base plate surface directed to the analyzer region, or a portion of the outer electrode coplanar with the base plate surface directed to the analyzer region.

DETAILED DESCRIPTION OF THE INVENTION

Figure 1:
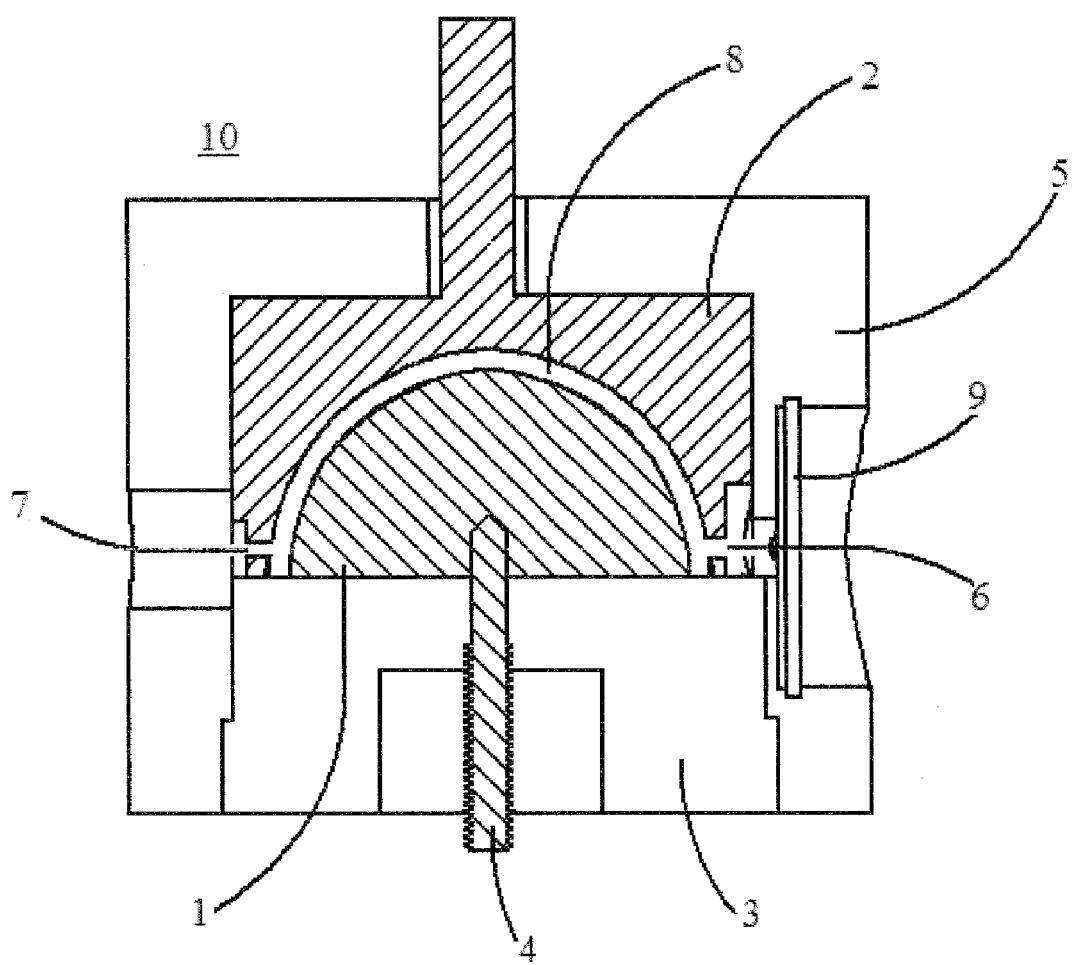
FIG. 1 shows a cross section of a hemispherical FAIMS according to an embodiment of the invention.

Embodiments of the invention are directed to partial ovoidal FAIMS devices where inner and outer electrodes have adjacent surfaces that are shaped as portions of ovoids that have been truncated by a plane that is on, parallel or perpendicular to a defining axis of symmetry for the ovoidal surfaces. The equivalent non-truncated ovoids may have high symmetry and may be ellipsoids or spheres. The equivalent non-truncated ovoid may be an egg shaped ovoid. The surfaces of both equivalent non-truncated ovoidal surfaces for the inner and outer electrodes have a common defining axis. The defining axis also determines the placement of at least one ion inlet and an ion outlet. All of many possible ion paths, through an analyzer region where an ion can traverse from the ion inlet to the ion outlet, are of essentially equal length and have essentially equal curvature.

In one embodiment of the invention, a single ion inlet and the ion outlet are through the outer electrode and have their centers residing on the defining axis when the truncating plane is parallel to the defining axis of the ovoidal surfaces and the ovoidal surfaces are those of more than a hemi-ovoid. In another embodiment of the invention, a single ion inlet and the ion outlet through the outer electrode have their centers residing on a line parallel to the defining axis of the ovoidal surface, where the line resides in a plane bisecting the partial ovoidal surfaces. The line is in the proximity of a base plate that seals the truncated planes of the electrodes where the truncated plane is on or parallel to the defining axis of the ovoidal surface and the partial ovoid is a hemi-ovoid, less than a hemi-ovoid, or more than a hemi-ovoid. For embodiments of the invention where the truncating plane is parallel to the defining axis, multiple inlets can be situated equidistant from a line between the center of the ion inlets and the ion outlet. The truncated planes are matched to the base plate, which supports and maintains a rigid and precise alignment between the separate surfaces of the inner and outer electrodes and seals the volume between the electrode surfaces, the volume defines an analyzer region between the ion inlets and outlet. The base plate electrically insulates the inner electrode from the outer electrode. In other embodiments of the invention a single inlet and a single outlet are situated in the base plate and in one embodiment of the invention are perpendicular to the defining axis or line parallel to the defining axis such that the ions need not turn upon introduction or removal from the analyzer region of the FAIMS device. In other embodiments of the invention, the inlet and outlet can allow ions to enter and exit at any angle relative the defining axis. In another embodiment of the invention, multiple ion inlets having separate channels or a single ion inlet having multiple channels deliver ions to the analyzer region at the base plate where the multiple ion channels are distributed evenly about the base plate, which is perpendicular to the defining axis of the ovoid and the ion outlet is through the outer electrode on the defining axis.

The partial ovoidal FAIMS design allows facile construction of a device that maintains the desired features of the known spherical side-to-side designs, but achieves precise and accurate electrode alignment of an inner ovoidal electrode with an outer ovoidal cavity electrode while delivering several thousand volts of RF to one of the electrodes. The partial ovoidal design allows precise rigid alignment by aligning and securing the inner and outer electrodes to a base plate.

Mounting of the electrodes to the base plate allow for a uniform alignment of the electrode surfaces. The tolerance for the displacement between the inner and outer electrodes that define the analyzer region should be high, and it is desirable that the displacement should not vary by more than 1 percent. The electrodes must be stable, allowing the field to be generated without arcing, yet the FAIMS must be sufficiently robust such that the electrodes are not damaged if arcing inadvertently occurs. Stable electrodes can comprise a metal or metal alloy, for example stainless steel. The two electrodes are generally, but not necessarily prepared from the same metal. The inner and outer electrodes can be hollow conductors, conductor coated conductors, or conductor coated insulators as long as the electrical connectors access the conductive surface of the electrodes. When the electrodes are metal coated substrates, the coating is of sufficient thickness and uniformity such that a continuous uniform metallic surface is presented to the analyzer region.

The base plate is an insulating material. The insulating material should be sufficiently rigid to maintain the alignment of the electrodes while in operation. A good insulating material for the base plate is thermally rigid such that heating during operation does not induce changes in the orientation of the electrodes. The base plate can be constructed from a rigid polymeric material, a glass, or a ceramic with a low vapor transmission and good thermal stability. Polymeric materials that can be used include polychlorotrifluoroethylene (PCTFE) and polyaryletherketone (PEEK). Machineable ceramics, for example MACOR, Mykroy, Mycalex or any non-porous ceramic can be used for the base plate.

A hemispherical FAIMS 10 is shown in FIG. 1 where an inner electrode 1 and an outer electrode 2 are fixed to a base plate 3. In this embodiment the inner electrode 1 is aligned and fixed to the base plate 3 by a threaded central electrical connection 4 to the inner electrode 1. In other embodiments of the invention the electrical connection need not be the structure for fixing the inner electrode to the base plate and neither the electrical connector nor a means to fix the inner electrode to the base need be on the center of the flat surface of the hemisphere. The outer electrode 2 is aligned and positioned with the inner electrode 1 in conjunction with a housing 5 that is matched to the base plate 3. Outer electrode 2 is fitted within housing 5 allowing it to be mounted on base plate 3 by securing housing 5 to base plate 3. The housing is not a requirement of the hemispherical FAIMS, and in alternate embodiments the outer electrode can be secured to the base plate by other means with or without a housing.

As shown in FIG. 1, an ion inlet 6 and an ion outlet 7 are adjacent to the base plate, each through the outer electrode 2 and housing 5 and separated from each other by a distance slightly less than the diameter of the spherical surface defining the concave hemispherical surfaces edge mounted to the base plate. All ions transported through the ion inlet 6 reach an analyzer region 8 defined by the volume between the concave and convex surfaces of inner electrode 1 and outer electrode 2. A nearly constant displacement occurs between any point on the convex surface and its nearest point of the concave surface. By having an asymmetric waveform, where the peak voltage during the high voltage portion of the waveform is called the dispersion voltage (DV), applied to either of the two electrodes and a constant compensation voltage (CV) applied to either electrode, differentiation of the ions can occur depending upon the applied CV.

By positioning the ion inlet 6 and ion outlet 7 very near the base plate in a plane bisecting the hemispherical surface of the outer electrode, all ions travel nearly an identical distance from the ion inlet 6 to the ion outlet 7. The ion inlet 6 receives the ions from an ion source, not shown, for introduction into the analyzer region 8. For example, the ion source can be an electrospray ionization ion source and a curtain plate electrode 9. Other non-limiting suitable ion sources include photoionization sources, atmospheric pressure MALDI, radioactivity based sources, corona discharge sources, and other rf-based discharge sources. A flow of a carrier gas directs the ions from the ion inlet 6 through the analyzer region 8 to the ion outlet 7.

During use, ions are produced in the gas phase for introduction into hemispherical FAIMS 10 from a suitable sample containing a species of interest. Typically, a mixture having a plurality of different ion types is produced when the sample is ionized. A potential gradient is used to accelerate the ions of the mixture from an ion source, through the curtain plate electrode 9 toward the ion inlet 6 where the ions become entrained in the carrier gas flow and are carried into the analyzer region 8. Once inside the analyzer region 8, the ions are carried through an electric field within the analyzer region 8 by application of the DV and the CV to inner electrode 1 and outer electrode 2. Ion separation occurs within the analyzer region 8 on the basis of the high field mobility properties of the ions. Those ions of the mixture that have a stable trajectory for a particular combination of DV and CV are selectively transmitted through the FAIMS analyzer region 8, whilst other ions of the mixture collide with an electrode surface and are lost. The selectively transmitted ions exit the analyzer region 8 through the ion outlet 7 and are typically subjected to detection or are otherwise analyzed.

In one embodiment of the invention the CV and DV can be applied to the inner electrode 1. In another embodiment of the invention the CV and DV can be applied to the outer electrode 2. In another embodiment of the invention the CV can be applied to inner electrode 1 and the DV can be applied to the outer electrode 2. In another embodiment of the invention the CV can be applied to outer electrode 2 and the DV can be applied to the inner electrode 1. Although inner electrode 1 is shown in FIG. 1 as a solid electrode of a single conducting material, in another embodiment of the invention the electrode can be a hollow electrode with or without a flat circular plate on the hemisphere as long as the electrical connector 4 makes electrical connectivity to the surface of the electrode. In another embodiment inner electrode 1 can be an insulator coated with a conductor with or without a flat circular plate of the hemisphere and with or without the circular plate being coated with the conductor, as long as electrical connectivity can be made between the electrical connector 4 and the conductive surface. In another embodiment inner electrode 1 can be one conductor coated with a second conductor coated on the first conductor at least on the convex surface. In like manner although outer electrode 2 is shown to be constructed as a solid single conductive material, in other embodiments of the invention, the outer electrode 2 can be hollow, be a first conductive material coated with a second conductor on the concave or entire surface, or an insulator coated with a conductive material where the conductive material is in electrical contact with an electrical connector.

Figure 2:
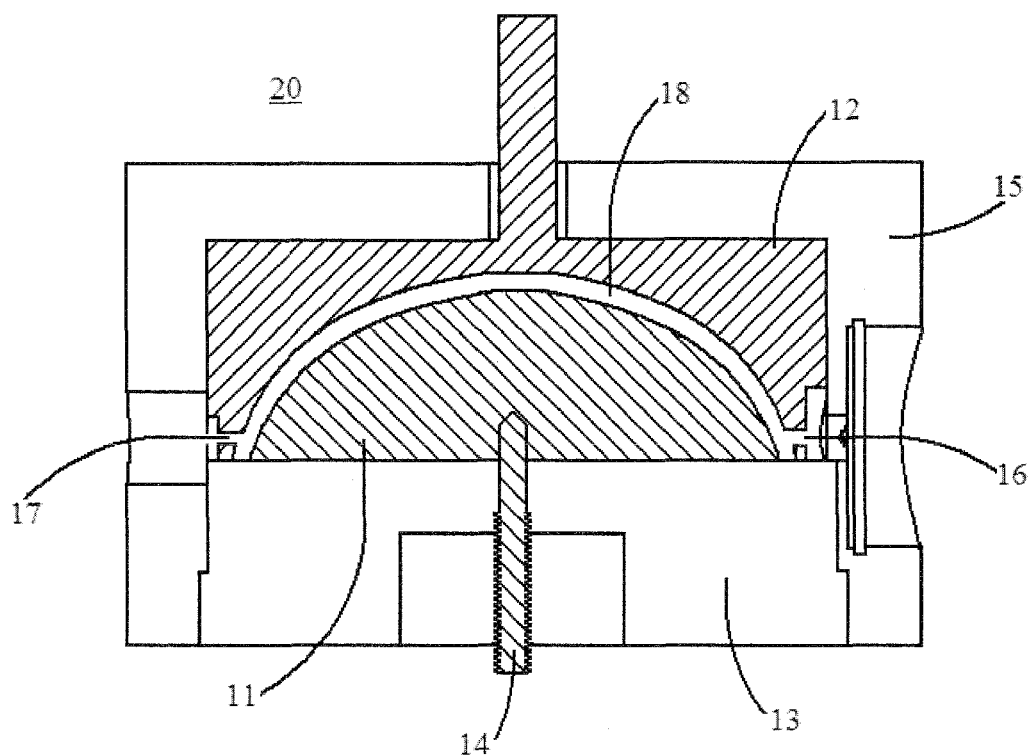
FIG. 2 shows a cross section of a hemi-elliptical FAIMS according to an embodiment of the invention.

In other embodiments of the invention an inner electrode can be a hemi-elliptical convex shaped electrode that is matched to a hemi-elliptical concave shaped electrode to give a nearly constant displacement between the partial ovoidal surfaces of the two electrodes. An exemplary symmetrical hemi-elliptical FAIMS 20 is shown in FIG. 2 where an inner electrode 11 and an outer electrode 12 are fixed to a base plate 13. In this embodiment the inner electrode 11 is aligned and fixed to the base plate 13 by an electrical connection 14 to the inner electrode 11, shown in FIG. 2 positioned midway on the long defining axis of the elliptical surface of the inner electrode. In other embodiments of the invention, the electrical connection need not be the structure for fixing the inner electrode to the base plate and neither the electrical connector nor a means to fix the inner electrode to the base plate need be on the long defining axis of the elliptical surface. The outer electrode 12 is aligned and positioned with the inner electrode 11 in conjunction with a housing 15 that is matched to the base plate 13. Outer electrode 12 is fitted within housing 15 allowing it to be mounted on base plate 13 by securing housing 15 to base plate 13. As with the hemispherical FAIMS, the housing is not a requirement of the hemi-elliptical FAIMS, and in alternate embodiments the outer electrode can be secured to the base plate by other means with or without the housing.

As shown in FIG. 2, an ion inlet 16 and an ion outlet 17 are adjacent to the base plate, each through the outer electrode 12 and housing 15 and separated from each other by a distance of nearly the long defining axis of the elliptical surface. With this orientation, all ions transported through the ion inlet 16 reach an analyzer region 18 defined by the volume between the concave and convex surfaces of inner electrode 11 and outer electrode 12. A nearly constant displacement occurs between any point on the convex surface and its nearest point on the concave surface. By having the DV applied to either of the two electrodes and the CV applied to the remaining electrode, differentiation of the ions can occur depending upon the applied CV.

By positioning the ion inlet 16 and ion outlet 17 very near the base plate and separated by the maximum distance of almost the long defining axis of the elliptical surface of the outer electrode, all ions travel nearly an identical distance from the ion inlet 16 to the ion outlet 17. The ion inlet 16 receives the ions from an ion source, not shown, for introduction into the analyzer region 18. A flow of a carrier gas directs the ions from the ion inlet 16 through the analyzer region 18 to the ion outlet 17.

Figure 3:
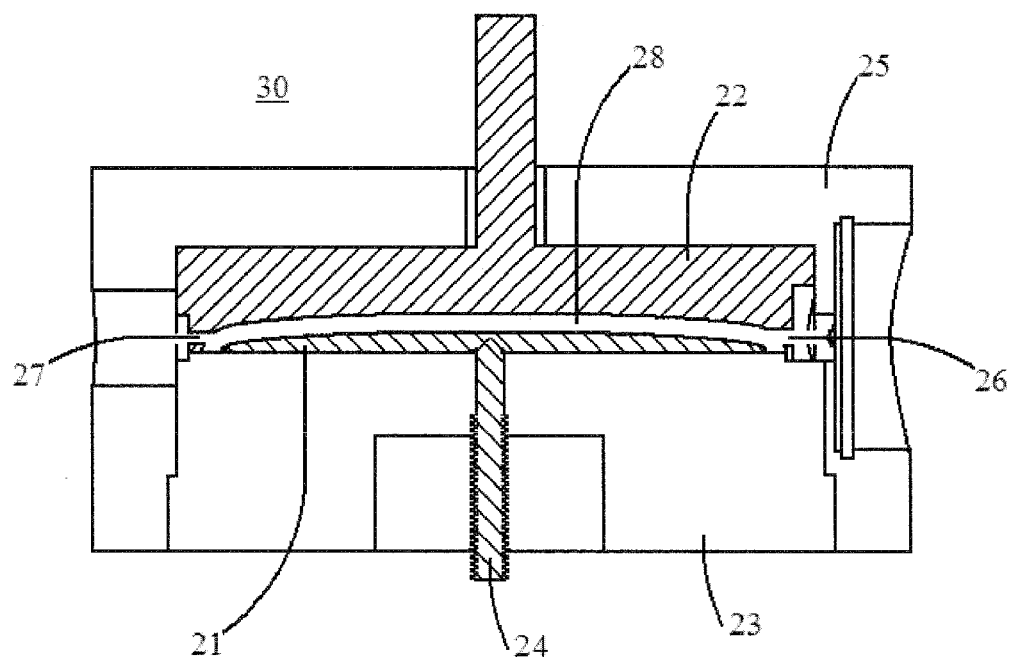
FIG. 3 shows a cross section of a hemi-elliptical FAIMS according to an embodiment of the invention with a small curvature through the majority of the analyzer region.

In an alternate embodiment shown in FIG. 3 a hemi-elliptical FAIMS 30 device is symmetrical, as is FAIMS device 20, however, the changing curvature of the inner electrode 21 and outer electrode 22 surfaces is very small for nearly the entire ellipse. The shape, curvature and dimensions of the inner and outer electrode surfaces can vary to achieve various resolution and sensitivity.

Figure 4:
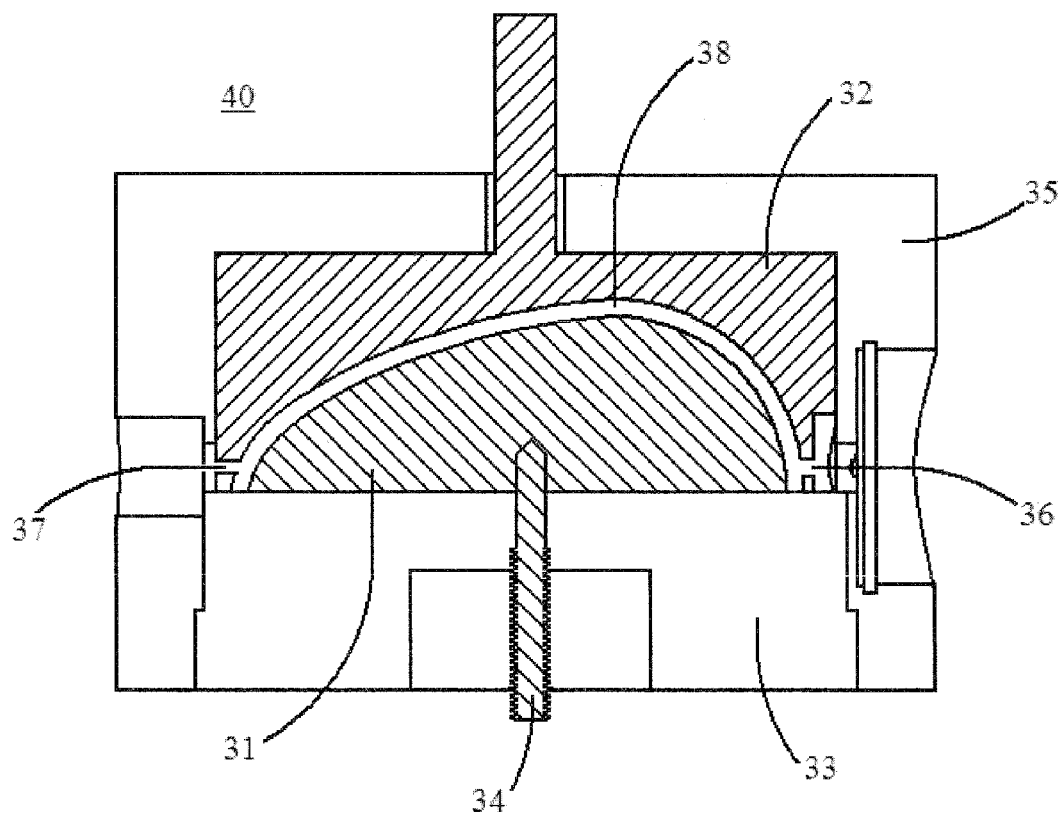
FIG. 4 shows a cross section of a hemi-ovoidal FAIMS according to an embodiment of the invention.

In an alternate embodiment, shown in FIG. 4, a hemi-ovoidal FAIMS 40 device is asymmetrical with respect to a plane normal to the truncated plane and includes the defining axis of the hemi-ovoidal surface. In hemi-ovoidal FAIMS 40, the electric fields are different at the ion inlet 36 region and at the ion outlet 37 region. For example, the radius of curvature of the surface of the inner electrode 31 in the vicinity of the ion inlet 36 is larger than the radius of curvature of the inner electrode 31 in the vicinity of the ion outlet 37. Accordingly, stronger focusing fields are created proximate the ion outlet 37. This relationship can improve the extraction efficiency from the analyzer region 38.

Figure 5:
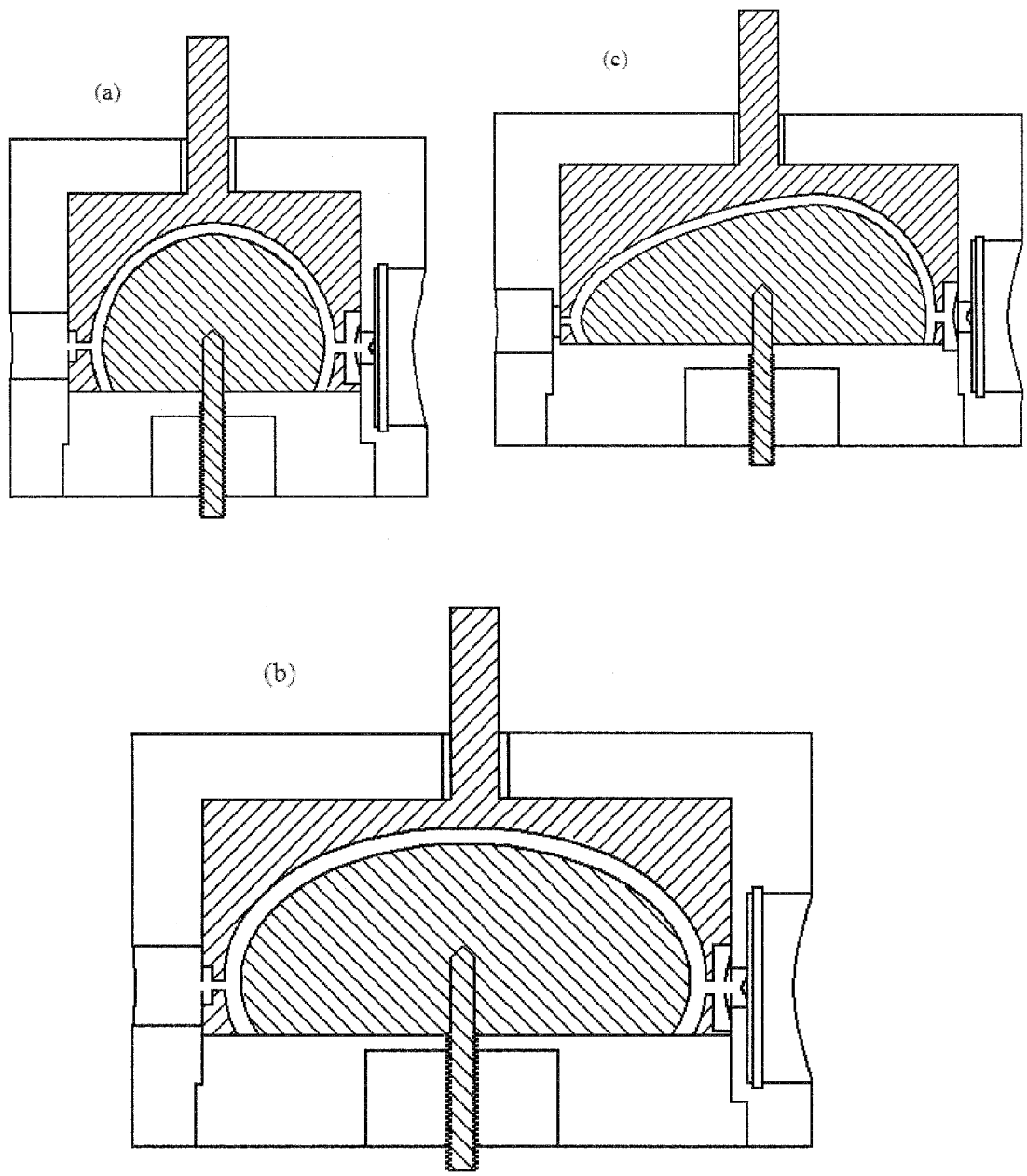
FIG. 5 shows cross sections of more than hemi-ovoidal FAIMS according to embodiments of the invention where the truncated ovoidal surfaces are: (a) spherical; (b) elliptical; and (e) egg shaped ovoidal.

In other embodiments of the invention the elliptical surfaces are truncated on a plane that is parallel to a defining axis of the truncated spheres, ellipsoids or ovoids. The plane of the outer electrode's surface has dimensions that are equal to or greater than the dimensions of the plane that includes the defining axis of the inner electrode's spherical, elliptical or ovoidal surface. In this manner, the ion inlet and ion outlet can be directly on the defining axis of the ovoid and the inner electrode can be placed into position for the FAIMS device where a one piece outer electrode is possible. Such FAIMS devices are illustrated in FIG. 5 that are (a) partial spherical, (b) partial elliptical, and (c) partial ovoidal in geometry. These designs increase the separation of the ion inlets and outlets from the base plate. In other embodiments, not shown, the plane of the outer electrode's surface can have dimensions that are less than the dimensions of the plane that includes the central axis of the inner electrode's spherical, elliptical or ovoidal surface when the outer electrode is constructed from two or more pieces.

Figure 6:
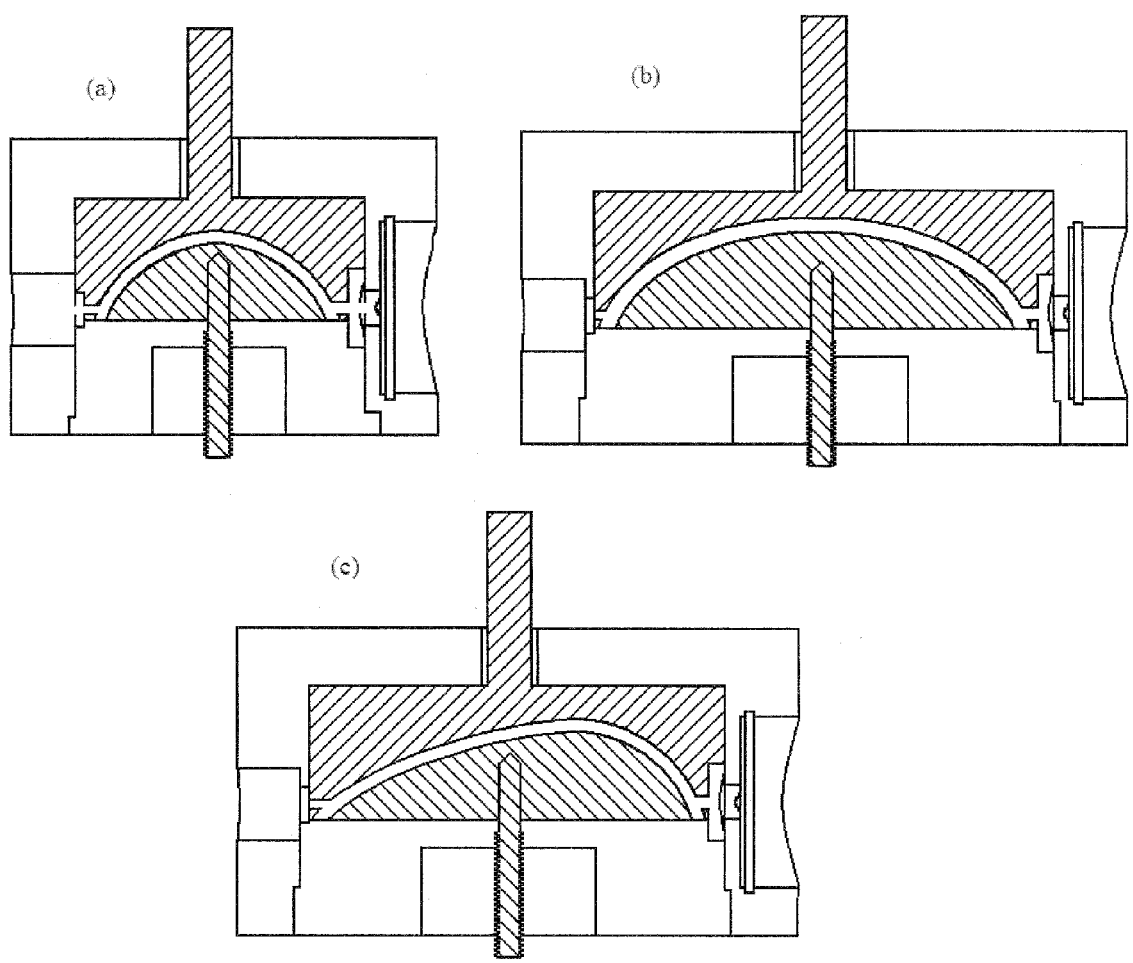
FIG. 6 shows cross sections of less than hemi-ovoidal FAIMS according to embodiments of the invention where the truncated ovoidal surfaces are: (a) spherical; (b) elliptical; and (c) egg shaped ovoidal.

In other embodiments of the invention, shown in FIG. 6, the truncated plane can be such that the defining axis for the ovoidal surfaces is not present in the electrodes as the electrodes have less than hemispherical, hemi-elliptical, or hemi-ovoidal surfaces. The line between the center of the ion inlet or inlets and ion outlet is contained in a plane perpendicular to the truncating plane of the ovoid and would contain the defining axis.

Figure 7:
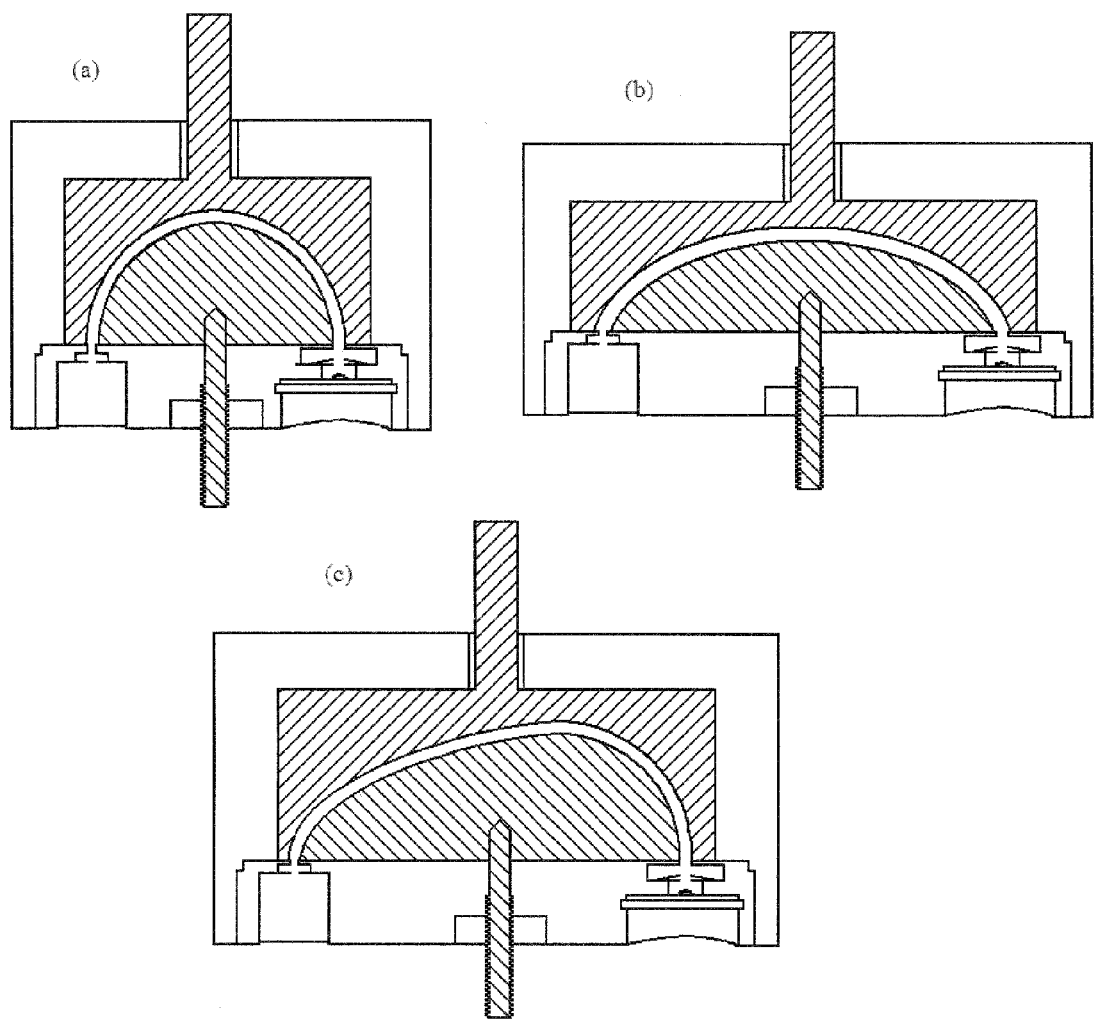
FIG. 7 shows cross sections of hemi-ovoidal FAIMS according to embodiments of the invention with inlets and outlets through the base plate perpendicular to the defining axis where the surfaces are: (a) hemispherical; (b) less than hemi-elliptical; and (c) egg shaped hemi-ovoidal.

In other embodiments of the invention a single ion inlet and a single ion outlet are situated through the base plate and are perpendicular to the defining axis of a ovoidal surface for a hemi-ovoidal device or the line parallel to the defining axis of the ovoidal surfaces when the less than hemi-ovoidal device, as shown in FIG. 7 for: (a) a hemispherical; (b) a less than hemi-elliptical; and (c) an egg shaped hemi-ovoidal FAIMS electrodes. The placement of the ion inlet and ion outlet through the base plate allows the introduction and removal of ions to the analyzer region without requiring an abrupt turn, for example a nearly 90 degree turn of the ion when introduced to the device illustrated in FIG. 1.

Figure 8:
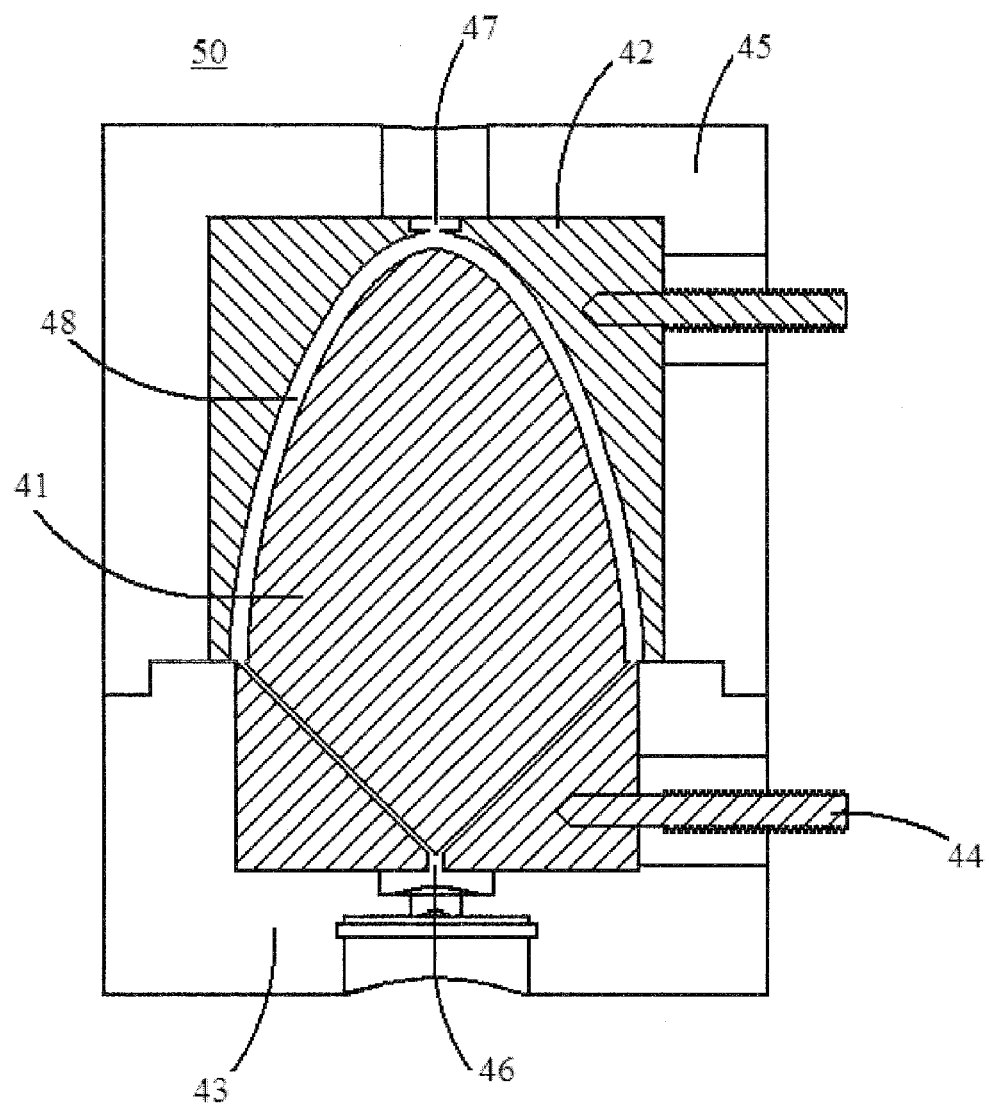
FIG. 8 shows a cross section of a hemi-elliptical FAIMS according to an embodiment of the invention with a multiple channel ion inlet through an extension of the inner electrode.

In another embodiment of the invention the hemi-ovoidal FAIMS device can have multiple ion inlets which include channels that originate at an orifice to receive ions and terminate at the truncating plane equidistant from the inner and outer electrodes ovoidal surfaces in or adjacent to the base plate. As shown in FIG. 8, in cross section, the hemi-elliptical FAIMS 50 has an ion inlet 46 with a multiplicity of channels, where the cross-section bisects two oppositely directed channels for delivering ions into the analyzer region 48 between the inner electrode 41 and the outer electrode 42. The ion inlet is built within an extension to the inner electrode such that the symmetric electric field within the electrode directs all of the ions through the channel. The ions are then carried with the carrier gas through the analyzer region 48 to a single ion outlet 47 through the outer electrode and situated on the defining axis of the ovoid. Again, multiplicities of ion paths through the analyzer region 48 are formed where the distances all ions travel from the ion inlet 46 channels to the ion outlet 47 are equal. In other embodiments, the ion inlet channels or multiple inlets can have channels that are integrated into the outer electrode or are not portions of either electrode but proceed through the base plate 43. As shown in FIG. 6, the base plate 43 in conjunction with a housing 45 fix and position the electrodes. The housing is not required, but can be a useful feature of the FAIMS device, and typically would be an insulating material.

Materials and Methods

Samples

Explosives were tested on a hemispherical FAIMS as illustrated in FIG. 1. The explosive analyzed were Trinitrobenzene (TNB), 2,4 Dinitrotoluene (2,4 DNT), 1,3 Dinitrobenzene (1,3 DNB) and Pentaerythritol tetranitrate (PETN+Cl). For example, a 10 ppm mixture of TNT and 3,4-DNT in 65/35 methanol/water was made.

Instrumentation

An alpha waveform generator (Ionalytics, Ottawa, Canada) was used to generate the 750 kHz asymmetric waveform. Data for comparison to the FAIMS device according to the invention was obtained using a Thermo FAIMS (Thermo-Fisher Scientific, San Jose, Calif.) with cylindrical geometry electrodes. Data were collected using a Thermo Finnigan LCQ quadrupole ion trap mass spectrometer and an Ionalytics GPI 1000 FAIMS system alpha prototype waveform generator. Ions were created by atmospheric pressure chemical ionization (APCI). All explosives analyzed were examined from a 10 ppm solution in 65:35 methanol:water unless otherwise noted. The APCI temperature was held at 75° C. and heated capillary of MS was held at room temperature. Analyte samples were infused at 15 μL/min A FAIMS device, as shown in FIG. 1, was constructed with inner and outer electrodes of stainless steel. The outer housing and base plate were made of Kel-F®, a polymer of chlorotrifluoroethylene to exploit its extremely low vapor transmission rate, excellent thermal characteristics and ability to maintain the wide operating temperature range of −400° F. to 400° F. The inner electrode has a radius of 0.5 in. and the analysis region had a gap of 0.0800±0.0005 in.

Results

Figure 9:
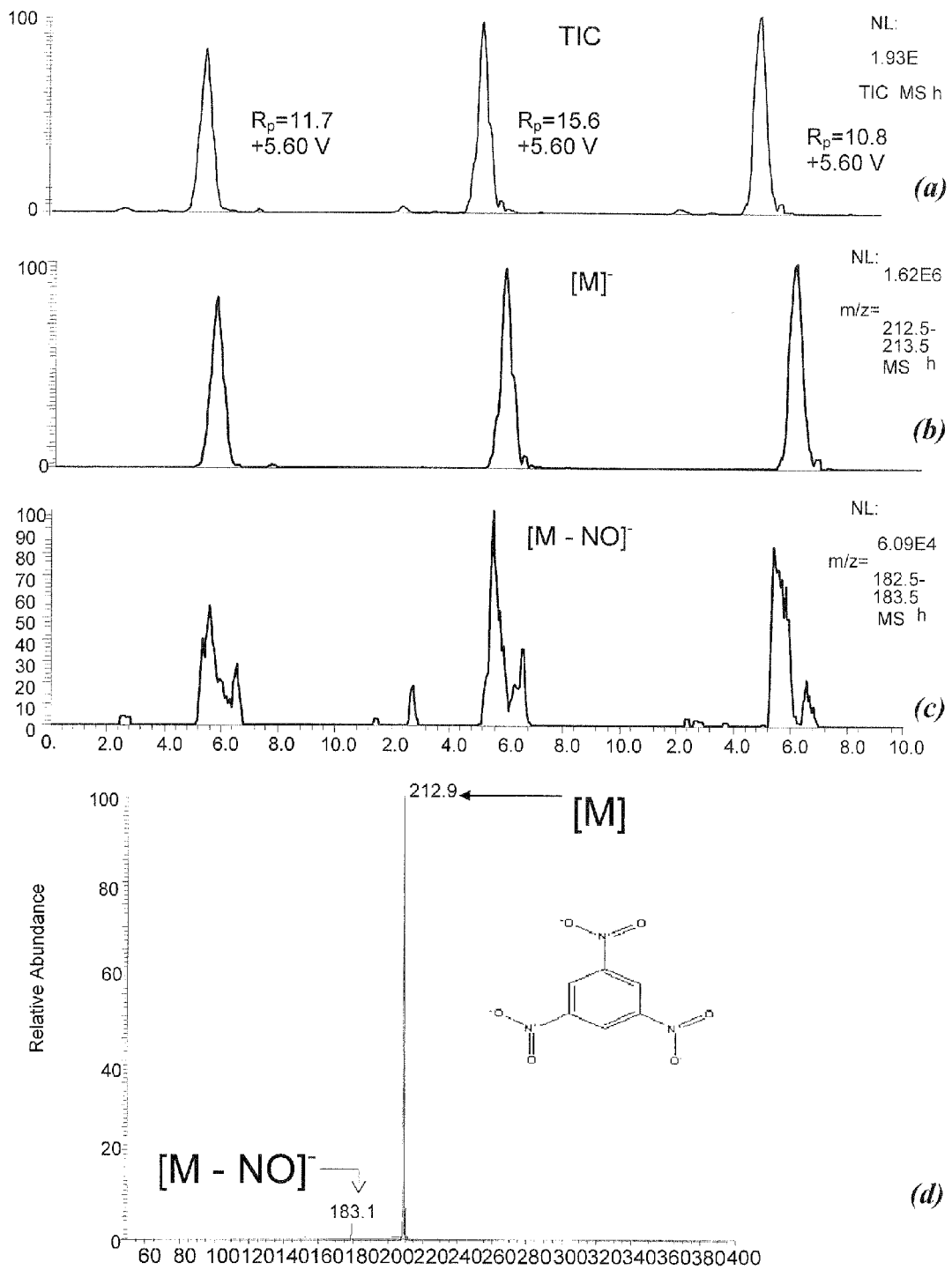
FIG. 9 shows three successive compensation voltage (CV) scans (a) and a mass spectrum (MS) (d) of Trinitrobenzene (TNB) using a hemispherical FAIMS. Intensities of total ion current (TIC) (a) and extracted chromatograms for m/z 213 (b) and 183 (c) are shown. Resolving power (Rp) and CVs are shown at each TIC peak.

FIG. 9 shows three successive CV scans, 9(a) and a MS 9(d) of Trinitrobenzene (TNB). The hemispherical FAIMS cell was used with the separation parameters being: DV=3214 V with a CV scan from 0 to +10 V over 2.5 minutes (4 V/min).

Intensities of total ion current (TIC) 9(a) and extracted chromatograms for m/z 213 9(b) and 183 9(c) are shown. Spectrum 9(d) displays an intensity of $1.91 \times 10^5$ counts (not shown). Resolving power (Rp) for each peak was calculated using Equation 1, below. CVs are also shown at each TIC peak.

$$R_p = CV/FWHM \quad \text{Equation 1}$$

Figure 10:
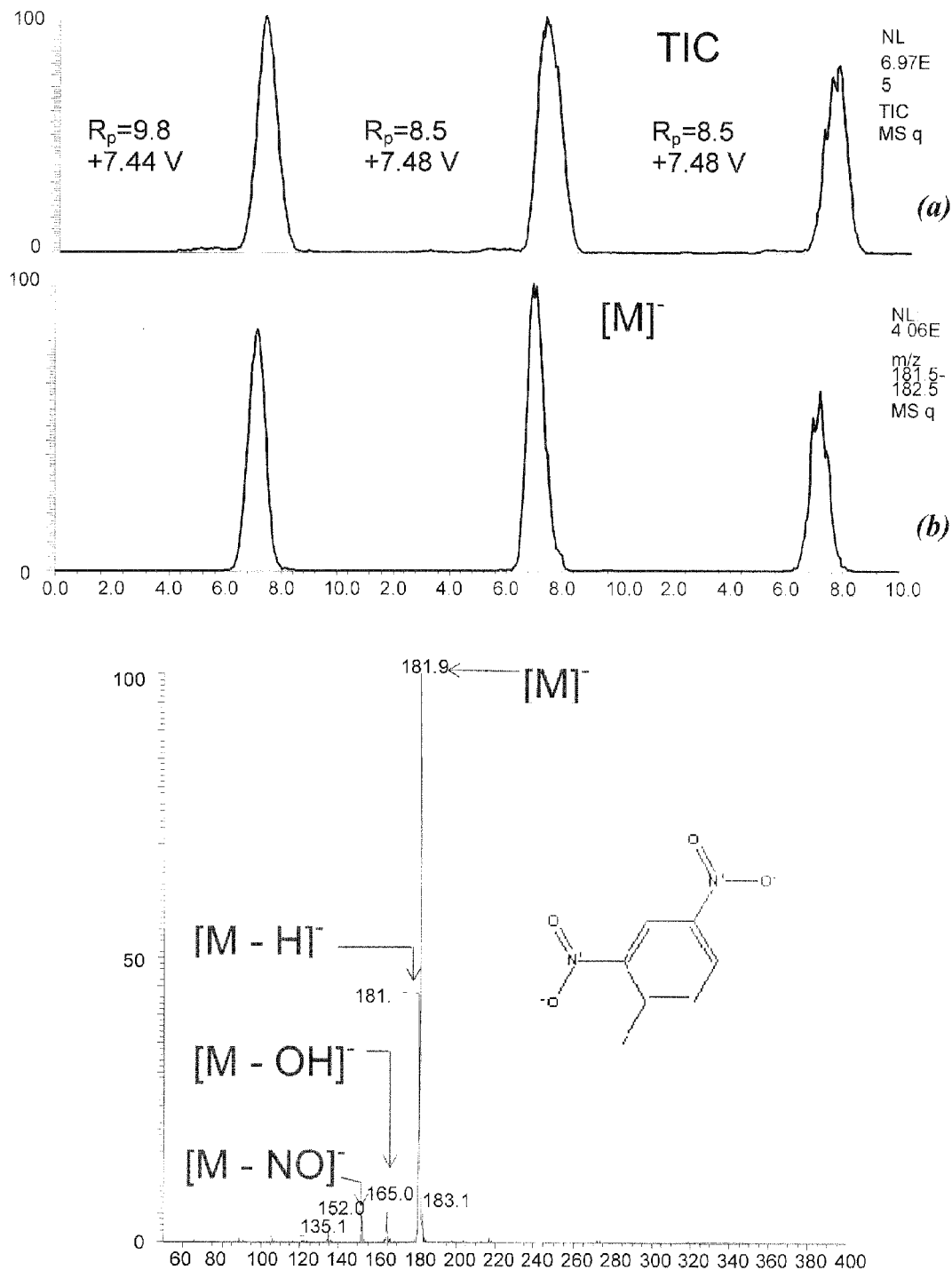
FIG. 10 shows three successive CV scans (a) and MS (c) of 2,4 Dinitrotoluene (2,4 DNT) using a hemispherical FAIMS. Intensities of TIC (a) and extracted chromatogram (b) are shown. Rp and CVs are shown at each TIC peak.

FIG. 10 shows three successive CV scans (left) and MS (right) of 2,4-Dinitrotoluene (2,4 DNT). Separation parameters are as those of TNB above. Intensities of TIC 10(a) and extracted chromatogram 10(b) are given on the figure. Spectrum 10(c) has an intensity of $4.86 \times 10^4$ counts (not shown). Rp and CVs are shown at each TIC peak and calculated using Equation 1, above.

Figure 11:
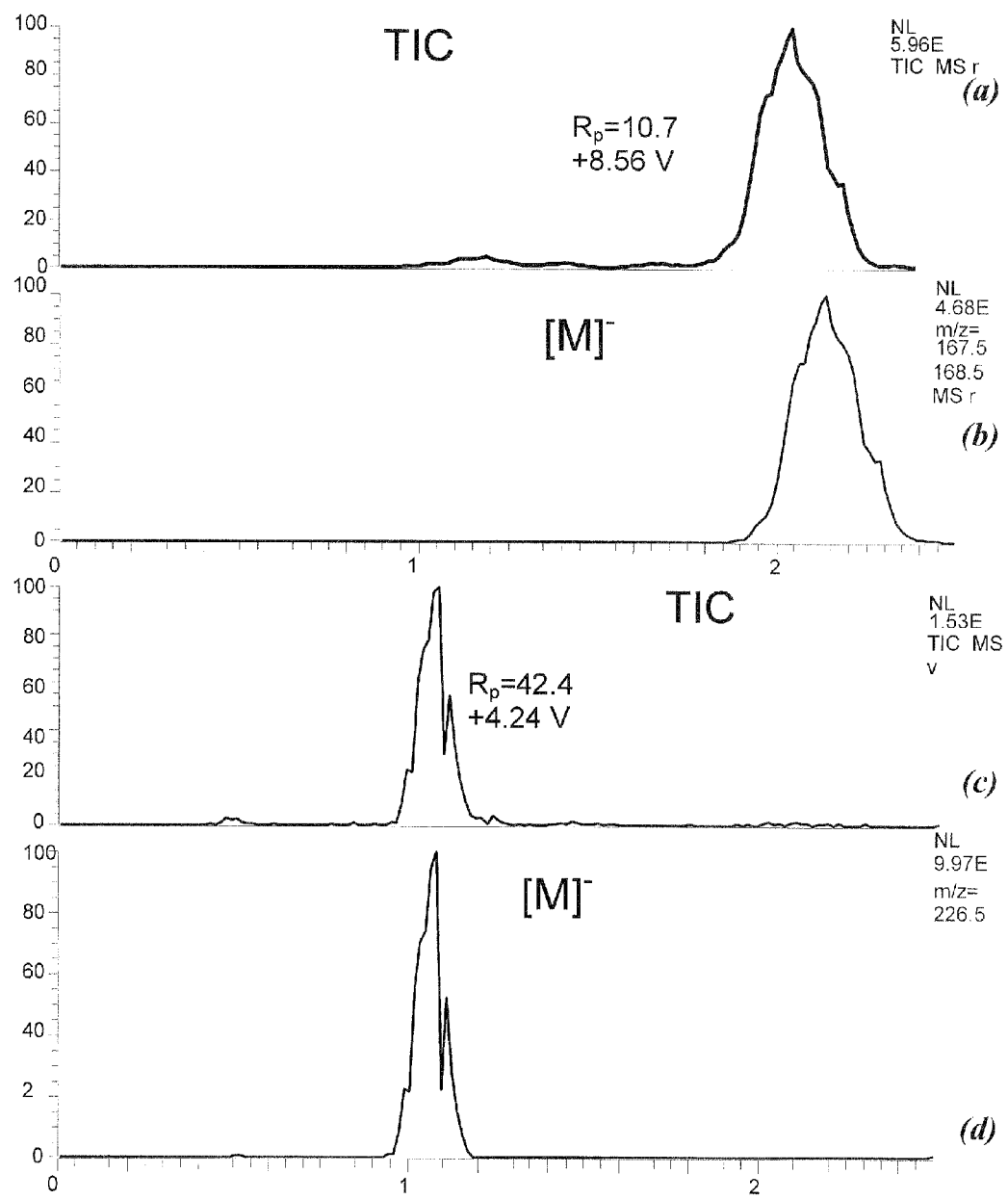
FIG. 11 shows CV scans of 1,3 Dinitrobenzene (1,3 DNB) (a) and Trinitrotoluene (TNT) (b) using a hemispherical FAIMS. Intensities of TIC and extracted chromatograms for 1,3 DNB (a) and (b) and TNT (c) and (d) are shown. Spectrum intensities, Rp and CVs are shown on each TIC peak. Mass spectra are shown for both 1.3 DNB (e) and TNT (f) with chemical structure.
Figure 11:
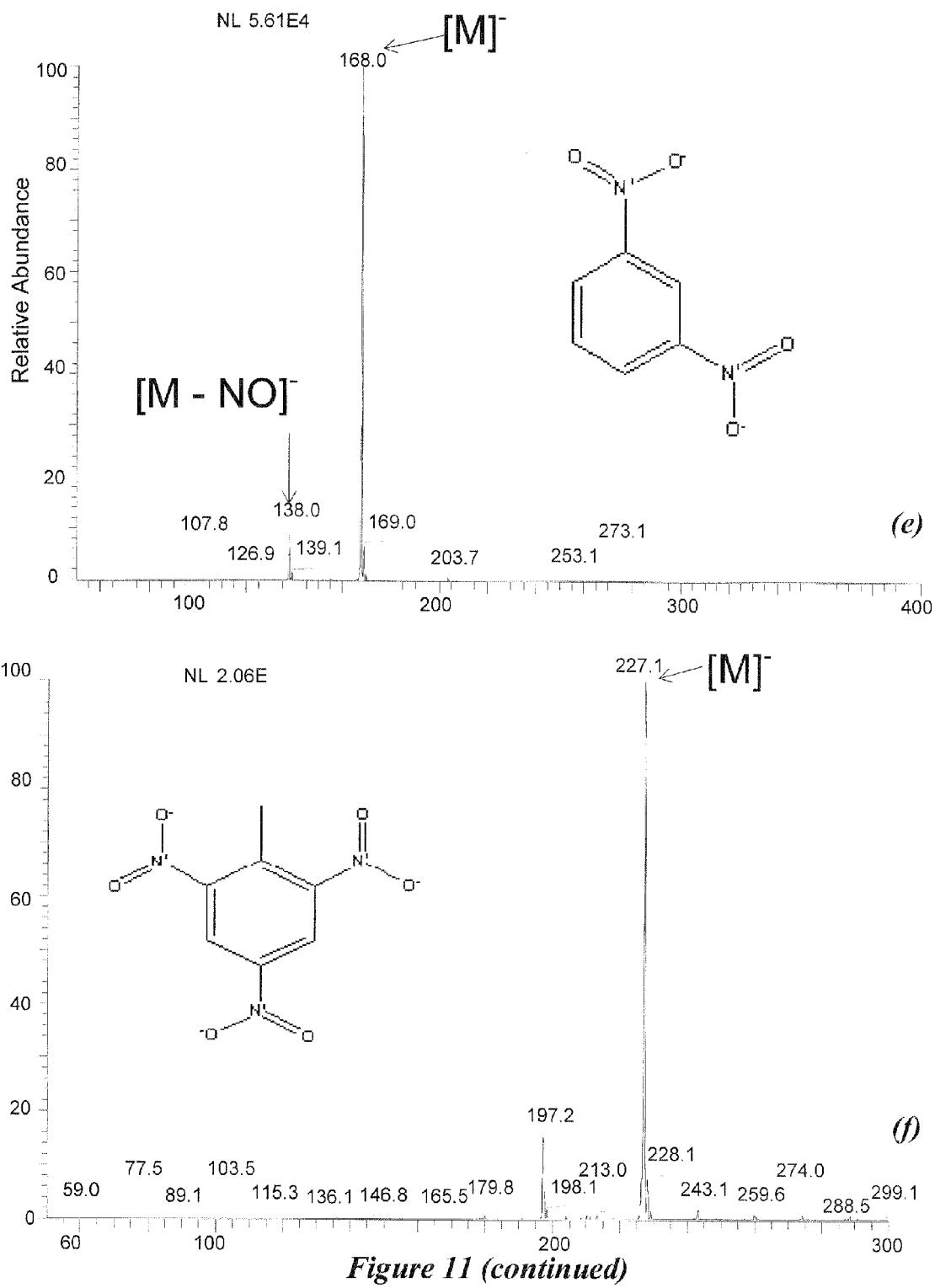

FIG. 11 shows CV scans of 1,3-Dinitrobenzene (1,3 DNB) and Trinitrotoluene (TNT) using the hemispherical FAIMS of FIG. 1. MS are shown for both (bottom with chemical structure). Separation parameters are similar to those given in above. Intensities of TIC and extracted chromatograms for 1,3 DNB 11(a) and 11(b) and TNT 11(c) and 11(d) are shown. Rp and CVs are shown at each TIC peak and calculated using Equation 1, above.

Figure 12:
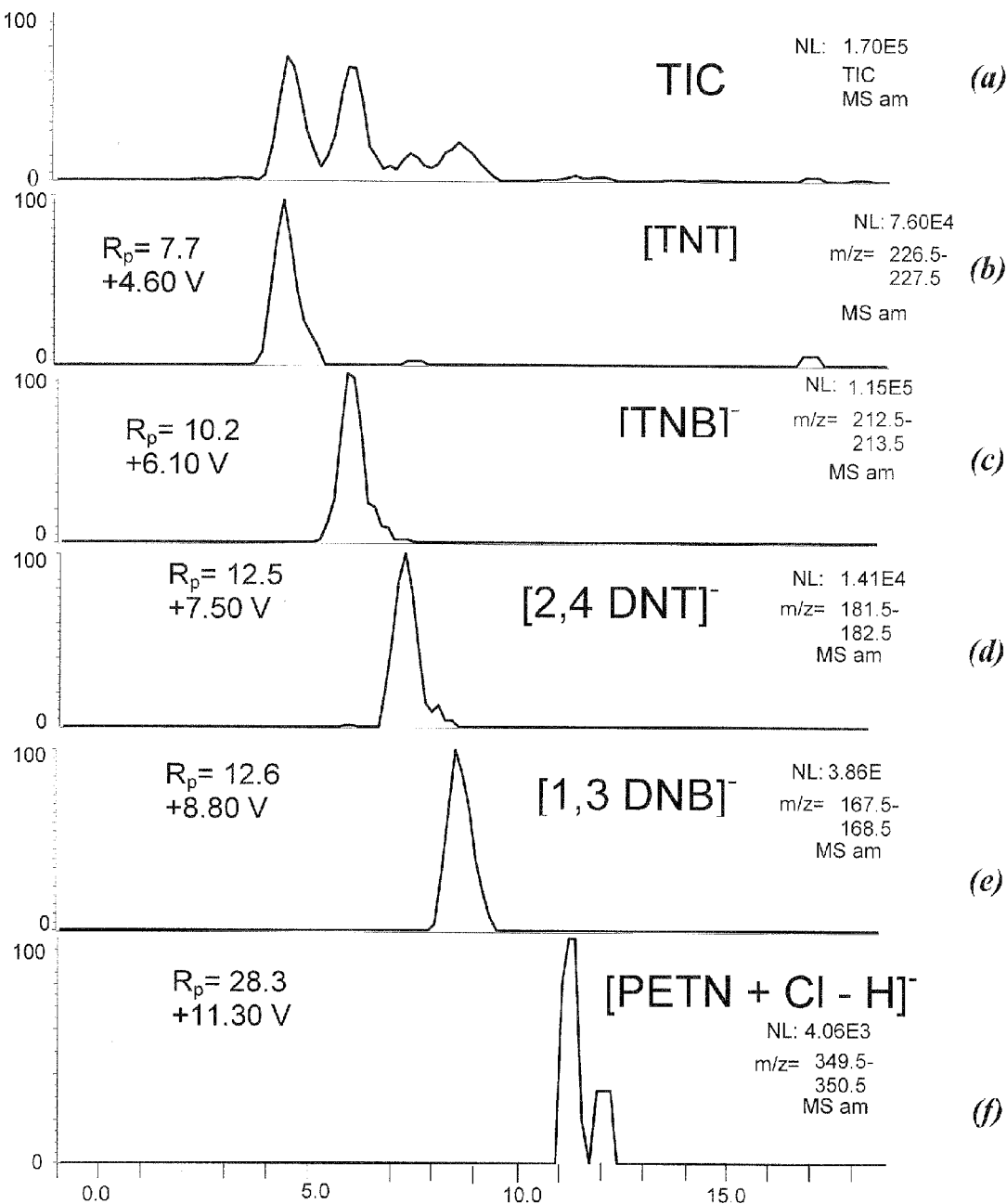
FIG. 12 shows CV scans of: TIC of a 2-ppm mixture (a) and extracted individual components of TNT (b), TNB (c), 2,4 DNT (d), 1,3 DNB (e) and Pentaerythritol tetranitrate (PETN+Cl) (f) using a hemispherical FAIMS. Intensities of TIC and extracted chromatograms, Rp and CVs, are adjacent to the traces. CV was scanned from −1 to +19 V over 2 minutes (10 V/min).

FIG. 12 shows CV scans of: TIC of a 2-ppm mixture 10(a) and extracted individual components of TNT 12(b), TNB 12(c), 2,4 DNT 12(d), 1,3 DNB 12(e) and Pentaerythritol tetranitrate (PETN+Cl) 12(f) using the hemispherical FAIMS of FIG. 1. Intensities of TIC and extracted chromatograms, $R_p$ and CVs, are adjacent to the traces. CV was scanned from −1 to +19 V over 2 minutes (10 V/min). The resolution, $R_s$, was calculated using Equation 2, below.

$$R_s = 2(CV_1 - CV_2)/(PW_{1\,10\%} + PW_{2\,10\%}) \quad \text{Equation 2}$$

Figure 13:
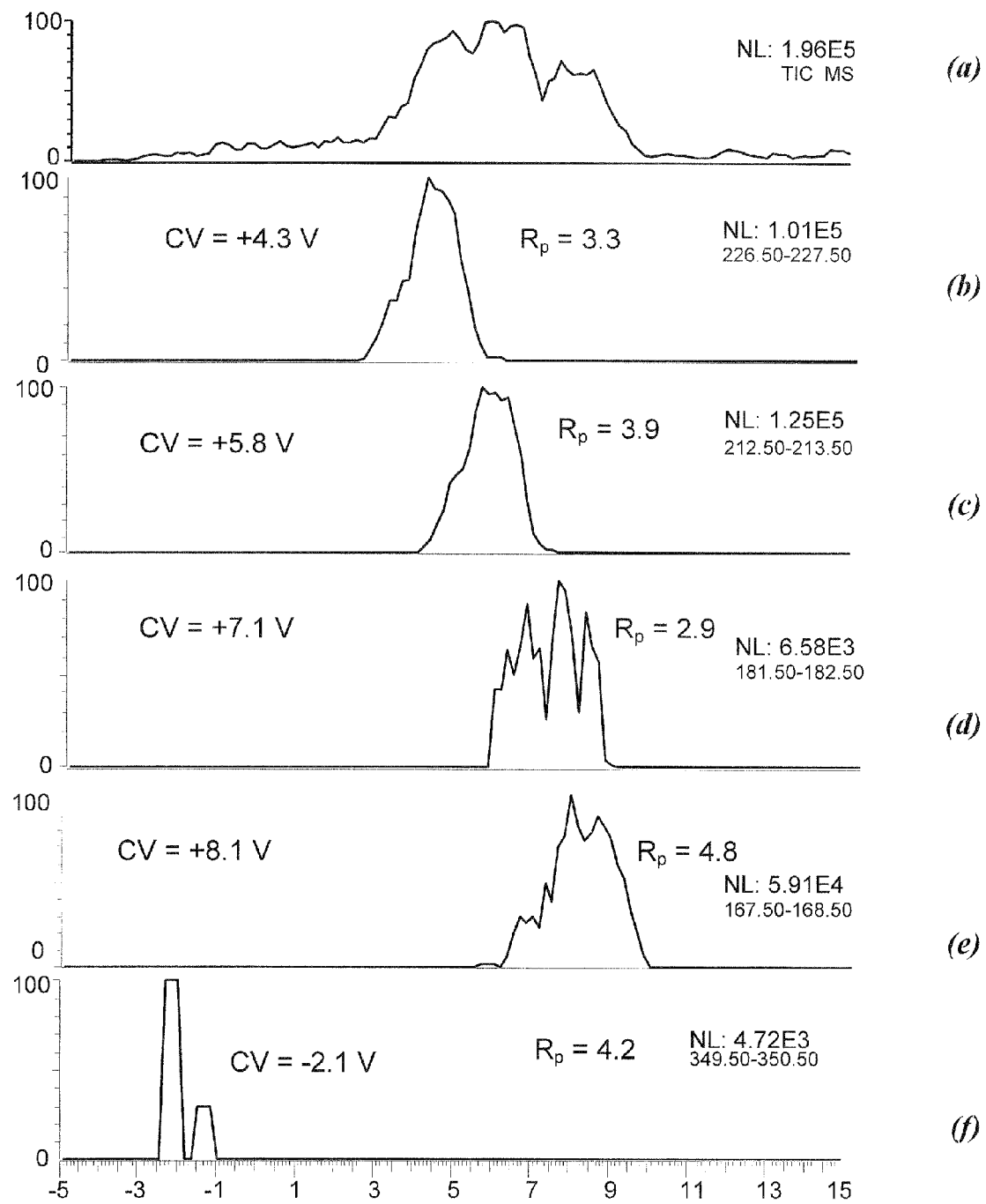
FIG. 13 shows CV scans of: TIC of a 2-ppm mixture $8(a)$ and extracted individual components of TNT $8(b)$, TNB $8(c)$, 2,4 DNT $8(d)$, 1,3 DNB $8(e)$ and Pentaerythritol tetranitrate (PETN+Cl) $8(f)$ using a prior art commercially available FAIMS.

Using a Thermo FAIMS the data of FIG. 13 was generated for the same explosives mixture used for the analysis carried out using the hemispherical FAIMS of FIG. 1 that is shown in FIG. 11. The CV's, $R_p$, and $R_s$ for the components using the commercially available FAIMS unit and that of the hemispherical FAIMS are given in Table 1, below. Commercial cell scanning parameters include a CV scan from −5 to +15 V over 2 minutes (10 V/min) at −4000 DV. $R_s$ and $R_p$ values are lower for the commercial cell, and some decrease in signal for the commercial cell occurred because of a brass capillary extender used with the cell. The bigger inner hemispherical electrode radius allows better resolution but with the price of decreased transmission, although, near-trapping potential wells near the ion outlet alleviates serious ion losses.

TABLE 1

Comparison between Commercial and Hemispherical Cells

| | Commercial Cell (16,000 V/cm) | | | Hemispherical Cell (16,072 V/cm) | | |
|---|---|---|---|---|---|---|
| | CV | Intensity | $R_s$ | CV | Intensity | $R_s$ |
| TNT | 4.33 | $1.37 \times 10^5$ | 3.33 | 4.24 | $9.97 \times 10^5$ | 8.80 |
| TNB | 5.47 | $1.37 \times 10^5$ | 4.45 | 5.60 | $1.62 \times 10^5$ | 12.7 |
| 1,3 DNB | 7.90 | $6.88 \times 10^4$ | 4.73 | 8.56 | $4.68 \times 10^5$ | 10.72 |
| 2,4 DNT | 7.33 | $7.64 \times 10^4$ | 4.07 | 7.46 | $4.06 \times 10^5$ | 8.90 |
| PETN + Cl | 0.27 | $2.04 \times 10^5$ | 0.09 | 8.15 | $1.02 \times 10^5$ | 1.27 |

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An apparatus for separating ions, comprising:
   at least one ion inlet;
   an ion outlet;
   an outer electrode comprising an inner concave partial ovoidal surface;
   an inner electrode comprising an outer convex partial ovoidal surface, said convex partial ovoidal surface concentric with said concave partial ovoidal surface, said convex surface's dimensions being less than said concave surface's dimensions providing a nearly constant displacement between said convex surface and said concave surface and wherein the volume between said concave surface and said convex surface defines an analyzer region extending between said at least one ion inlet and said ion outlet;
   an electrical contact on at least one of said outer electrode and said inner electrode for applying a compensation voltage to said outer electrode and said inner electrode, and an electrical contact on the other of said outer electrode and said inner electrode for applying an asymmetric waveform to at least one of said outer electrode and said inner electrode wherein during application of said compensation voltage and said asymmetric waveform at least one ion is selectively transmitted through said analyzer region from said at least one ion inlet to said ion outlet in one or more equivalent curved paths imposed by the shape of said partial ovoidal surfaces defining said analyzer region; and
   a base plate comprising a material wherein said electrodes are fixed and electrically insulated from each other.

2. The apparatus of claim 1, wherein said ovoidal surfaces comprise spherical surfaces, elliptical surfaces, or egg shaped ovoidal surfaces.

3. The apparatus of claim 1, wherein said partial ovoidal surfaces are greater than hemi-ovoidal surfaces.

4. The apparatus of claim 3, wherein said at least one ion inlet that resides in a first portion of said outer electrode and said ion outlet resides in a second portion of said outer electrode wherein said ion outlet is on a common defining axis of said ovoidal surfaces and said at least one ion inlet is situated on or are equidistant about said common defining axis of said ovoidal surfaces.

5. The apparatus of claim 1, wherein said partial ovoidal surfaces are less than or equal to hemi-ovoidal surfaces.

6. The apparatus of claim 5, wherein said at least one ion inlet that resides in a first portion of said outer electrode and said ion outlet resides in a second portion of said outer electrode wherein said ion outlet is on a common defining axis of said ovoidal surfaces and said at least one ion inlet is situated on or are equidistant about a line proximal to said base plate and parallel to said common defining axis of said ovoidal surfaces in a bisecting plane of said partial ovoidal surfaces.

7. The apparatus of claim 1, wherein said ion inlet resides in a first portion of said base plate and said ion outlet resides in a second portion of said base plate, wherein said ion inlet and said ion outlet reside outside of said outer electrode.

8. The apparatus of claim 7, wherein said ion inlet and said ion outlet are perpendicular to a line that is parallel to a common defining axis of said partial ovoidal surfaces or, when said partial ovoidal surfaces are hemi-ovoidal surfaces, are perpendicular to a common defining axis of said hemi-ovoidal surfaces.

9. The apparatus of claim 1, wherein said at least one ion inlet comprises a plurality of ion inlet channels exiting into said analyzer region at a plane of truncation of said partial ovoidal surfaces at said base plate and said ion outlet resides in a portion of said outer electrode on a common defining axis of said ovoidal surfaces perpendicular to said plane of truncation.

10. The apparatus of claim 9, wherein said ion inlet channels are at least partially through said base plate.

11. The apparatus of claim 9, wherein said ion inlet channels are at least partially through said inner electrode.

12. The apparatus of claim 9, wherein said ion inlet channels are at least partially through said outer electrode.

* * * * *

UNITED STATES PATENT AND TRADEMARK OFFICE
CERTIFICATE OF CORRECTION

PATENT NO. : 8,237,118 B2  Page 1 of 1
APPLICATION NO. : 12/195867
DATED : August 7, 2012
INVENTOR(S) : Todd A. Prox et al.

It is certified that error appears in the above-identified patent and that said Letters Patent is hereby corrected as shown below:

Column 2,
Line 37, "effective" should read --effectively--.

Column 3,
Lines 38-39, "hemi-ovoidal surfaces" should read --hemi-ovoidal surface--.
Line 40, "hemi-ovoidal surfaces" should read --hemi-ovoidal surface--.

Column 4,
Line 25, "FAIMS. Intensities of" should read --FAIMS. Spectra are shown for both (bottom with chemical structure). Intensities of--.

Column 5,
Line 40, "allow for" should read --allows for--.
Line 43, "that define" should read --that defines--.

Column 9,
Line 35, "explosive analyzed" should read --explosives analyzed--.
Line 54, "at 15 μL/min" should read --at 15 μL/min.--.
Line 66, "DV=3214" should read --DV=-3214--.

Signed and Sealed this
Twenty-third Day of October, 2012

David J. Kappos
*Director of the United States Patent and Trademark Office*